United States Patent [19]

Henderson

[11] 4,236,008
[45] Nov. 25, 1980

[54] FLUORINATION OF PRECURSORS FOR FLUORINE ANALOGS OF HYDROCODONE AND OXYCODONE

[75] Inventor: Rosetta M. Henderson, Wilmington, Del.

[73] Assignee: E. I. Du Pont de Nemours and Company, Wilmington, Del.

[21] Appl. No.: 944,198

[22] Filed: Sep. 19, 1978

[51] Int. Cl.$^3$ .......................................... C07D 489/00
[52] U.S. Cl. ..................................................... 546/46
[58] Field of Search ...................... 546/46, 74; 424/260

[56] References Cited

U.S. PATENT DOCUMENTS

| | | | |
|---|---|---|---|
| 3,137,701 | 6/1964 | Ayer | 546/46 |
| 3,332,950 | 7/1967 | Blumberg et al. | 546/45 |
| 3,393,197 | 7/1968 | Pachter et al. | 546/44 |
| 3,928,359 | 12/1975 | Walther et al. | 546/45 |
| 3,976,691 | 8/1976 | Middleton | 260/44 F |
| 4,089,855 | 5/1978 | Chatterjie et al. | 546/44 |

OTHER PUBLICATIONS

Somogyi, et al., Chemical Abstracts, vol. 87, 168240y (1977).
Bognar, et al., Chemical Abstracts, vol. 77, 19840k (1972).
Makleit, et al., Chemical Abstracts, vol. 77, 152405p (1972).
Makleit, et al., Chemical Abstracts, vol. 84, 90359k (1976).
Bognar, et al., Chemical Abstracts, vol. 73, 131174q (1970).
Yeh, et al., Journal of Pharmaceutical Sciences, vol. 65, pp. 902–904 (1976).
Bognar, et al., Acta Chimica Academiae Scientiarum Hungaricae, vol. 67 (1), pp. 63–69 (1971).
Stork, et al., J. Am. Chem. Soc., vol. 78, pp. 4619–4621 (1956).
Middelton, J. Org. Chem., vol. 40, pp. 574–578 (1975).
Markovskij et al., Synthesis, Communications, pp. 787–789 (1973).

*Primary Examiner*—Donald G. Daus
*Assistant Examiner*—Diana G. Rivers

[57] ABSTRACT

Process of reacting hydrocodone or oxycodone salt or amide with a fluorinating agent to obtain fluorinated derivatives.

8 Claims, No Drawings

FLUORINATION OF PRECURSORS FOR FLUORINE ANALOGS OF HYDROCODONE AND OXYCODONE

DESCRIPTION

Technical Field

This invention relates to a fluorination process for production of precursors for fluorine analogs of hydrocodone and oxycodone. The latter exhibit analgesic and/or narcotic antagonist properties in mammals.

Background Art

Morphine and codeine analgesics exhibit toxic properties or have addictive action. Considerable effort has been made to find derivatives that are free from these qualities and still have analgesic effects. Compounds which are narcotic antagonists are also useful in medicine, such as treatment of addicts.

Fluorine derivatives of codeine have been reported by Ayer U.S. Pat. No. 3,137,701 from the reaction of a 6-hydroxyalkaloid having the codeine ring structure with a fluorinating agent such as N-(2-chloro-1,1,2-trifluoroethyl)diethylamine. The compound obtained by Ayer, and confirmed by Bognar et al., Acta Chimica Academiae Scientiarum Hungaricae 67, 63–69 (1971), has the formula

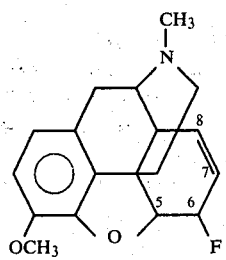

wherein the double bond is at the 7,8 carbon position, i.e. beta-gamma, relative to fluorine in the 6-position. It is well-known that fluorine substitution in organic compounds causes different biological effects and is different from chlorine, bromine or iodine substitution, as for example the 6-chloro, 7-8 double bond compound disclosed by Stork et al., J. Am. Chem. Soc. 78, 4619 (1956).

According to published reports, "diethylaminosulfur trifluoride (DAST) is a convenient reagent for replacing the carbonyl oxygen of aldehydes and ketones with two fluorine atoms." W. J. Middleton, J. Org. Chem., 40, 574 (1975), "New Fluorinating Reagents, Dialkylaminosulfur Fluorides." L. N. Markovskij, V. E. Pashinnik, and A. V. Kirsanov, Synthesis, 787 (1973). Middleton used $CCl_3F$, diglyme, methylene chloride, and benzene as reaction solvents and temperatures from 25° to 85° C. The Russian Workers used no added solvents; the carbonyl compound and dialkylaminosulfur trifluoride were simply mixed in equal molar amounts and heated. In accordance with the process of the invention, many cyclic and acyclic ketones are transformed by DAST into vinyl fluorides as well as gem-difluorides.

Disclosure of the Invention

A compound of the formula

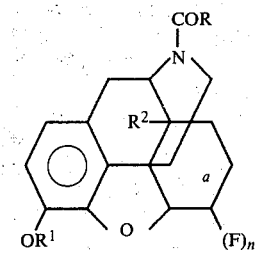

wherein

R is selected from the group consisting of alkyl of 1–5 carbon atoms, vinyl, 1-propenyl, isobutenyl, cycloalkyl of 3–6 carbon atoms, furanyl, thienyl, thienylmethyl and phenylmethyl which may be ring substituted with chloro, bromo, fluoro, or 1–3 carbon atom alkyl substituents;

$R^1$ is selected from the group consisting of alkyl 1–4 carbon atoms, alkanoyl of 1–4 carbons;

$R^2$ is selected from the group consisting of hydrogen, fluorine, hydroxy and alkanoyloxy of 1–4 carbon atoms;

n is 1 or 2; and a is a 6,7 double bond when n=1, and a single bond when n=2.

The compounds (I) can be prepared by reacting

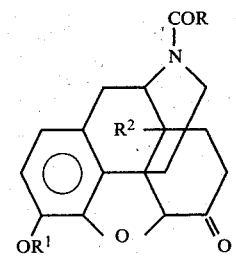

wherein R, $R^1$ and $R^2$ are as defined above with a disubstituted aminosulfur trifluoride of the formula $R^3R^4NSF_3$ wherein each $R^3$ and $R^4$, alike or different, is a primary alkyl group of 1–4 carbon atoms; or when taken together are —$(CH_2)_4$—, —$(CH_2)_5$— or —$CH_2CH_2OCH_2CH_2$—; at a temperature of about −40° C. to about +80° C.; in the presence of a polar or nonpolar solvent and recovering a fluorine containing compound. When $R^2$ is to be hydroxyl in the final product, the compound subjected to fluorination should have $R^2$ as the ester (or equivalent protective group) which is subsequently converted to the hydroxyl.

The production of pharmaceutically active compounds of the type

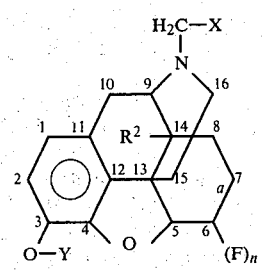

where

X is H or R

Y is H or $R^1$

R, $R^1$, $R^2$, n and a are as defined above and pharmaceutically acceptable salts of the compounds such as the hydrochloride, sulfate, phosphate, nitrate, citrate, maleate and the like, is accomplished by subjecting I to reduction wherein the —NCOR group is converted to —NCH$_2$R. The reduction can be accomplished by usual chemistry, as for example, subjecting the intermediate I to reaction with LiAlH$_4$, as exemplified in the examples below. Other reducing agents which can be used include alkali metal hydrides such as sodium or potassium borohydride.

Compounds III may also be prepared in accordance with the present invention by reacting

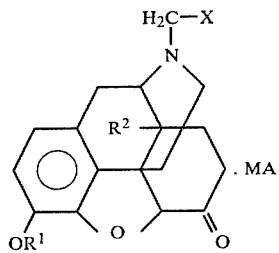

IV wherein X, R, $R^1$ and $R^2$ are as defined above and MA signifies a mineral acid, compound IV thus being a mineral acid salt, with a disubstituted aminosulfur trifluoride of the formula $R^3R^4NSF_3$ all as described above.

The mineral acid (MA) salt of compounds III wherein Y is $R^1$ may be represented by the formula

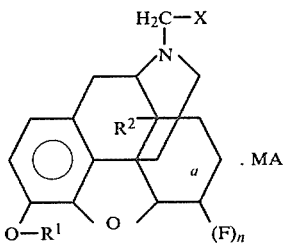

V wherein X, R, $R^1$, $R^2$, a and n are as defined above. In the compounds III which are obtainable by the procedures of this invention the substituent in the 3-position is generally the 3—OCH$_3$ substituent. As will be more fully described hereinafter, compounds III having substituents —OY other than —OCH$_3$ in the 3-position are obtainable from compounds III having the 3—OCH$_3$ substituent using general synthetic methods.

When $R^2$ is OH in starting compounds I or IV the use of excess fluorinating agent, dialkylaminosulfur trifluoride, results in a compound III where $R^2$=F.

The disubstitutedaminosulfur trifluorides are known compounds. Particularly useful are diethylaminosulfur trifluoride (DAST), pyrrolidinosulfur trifluoride, morpholinosulfur trifluoride and piperidylsulfur trifluoride.

The reaction is normally carried out in a solvent medium, preferably with use of a highly polar catalyst. The solvents can be polar or nonpolar but must be nonreactive with the aminosulfur trifluoride. Polar solvents tend to give more of the 6-fluoro-6,7-unsaturated codeines (n=1) while nonpolar solvents generally give more of the 6,6-difluoro compounds (n=2).

By polar solvent is meant a compound that has a high dielectric constant. Solvents which favor conversion of ketones to vinylene fluorides (>C=CF—) are polar and include dioxane, diethyl ether, tetrahydrofuran, ethylene glycol dimethyl ether, diethylene glycol dimethyl ether, and triethylene glycol dimethyl ether, etc. Nonpolar solvents such as hydrocarbons and halogenated hydrocarbons generally increase the amount of 6,6-difluoro (gem) compound formed.

The addition of a small amount of a strong acid as a highly polar catalyst, such as fuming sulfuric acid, increases the rate of formation of the 6,7-unsaturated-6-fluoride. Other useful catalysts are strong mineral acids that in the quantities used do not react with the carbonyl compound or with double bonds or other groups of the codeine-type compounds. Useful catalysts include perchloric, polyphosphoric, fluosulfonic acid, etc. The useful ones generally have a log Ka or more than about −2. The amount of catalyst is generally of the order of 0.001 to 1% by weight of the starting ketone. The catalyst is believed to function to increase the polarity of the reaction media and increase the rate.

The reaction is conducted under substantially anhydrous conditions. The reaction vessel is suitably glass but metal or ceramic containers can be used. The reaction is conducted at −40° to about +80° with the range 0° to 30° being generally preferred. The time is dependent upon the reactants and the temperature, with times of from less than an hour to a week or more being useful. Pressure is not critical but ambient or autogenous pressure is preferred.

The fluoro compounds obtained can be separated from the reaction mixture by conventional procedures. Chromatography is a particularly useful procedure for separation and purifications but crystallization, extraction, etc. can be used.

All temperatures reported herein are in °C.

Best Mode

The best mode of practicing the invention is exemplified by Example 6.

EXAMPLE 1

17-Methyl-6,7-didehydro-4,5-epoxy-6-fluoro-3-methoxymorphinan Hydrochloride (2) and
17-Methyl-6,7-dihydro-4-hydroxy-5-chloro-6-fluoro-3-methoxymorphinan Hydrochloride (3)

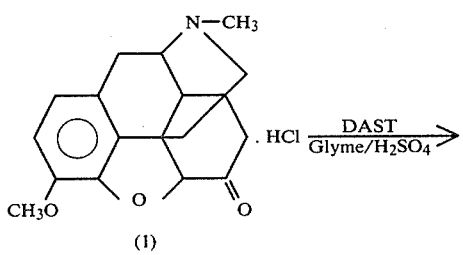

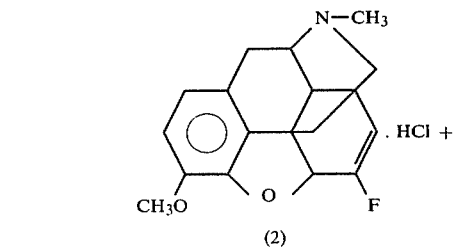

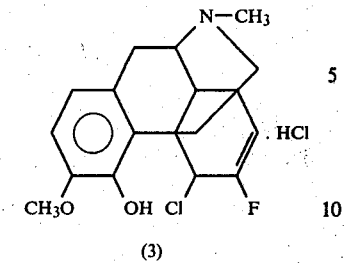

(3)

A solution of 40 ml of diethylaminosulfur trifluoride (DAST) in 160 ml of glyme was added dropwise to a suspension of 8.0 g of hydrocodone hydrochloride and 1.6 ml of fuming sulfuric acid in 240 ml of glyme cooled to −78°. The reaction mixture was warmed to room temperature and stirred for 8 days. The mixture was poured over ice, made basic with sodium bicarbonate and extracted with methylene chloride. Evaporation of the methylene chloride extracts gave a viscous oil which was taken in ether and filtered. Concentration of the ether filtrate gave 4.87 g of a white solid which was chromatographed on silica. Elution with 1/1 hexane/acetone containing 1% diethylamine gave 0.58 g of white solid (2) melting at 167°–169° (HCl salt 214°–217°) and 2.09 g of white solid (3) melting at 169°–173°. (HCl salt 178°–182°). The infrared spectrum showed =CF absorption at 5.91μ with no indication of C=O. $^{19}$F nmr (CDCl$_3$) for (3) δ−116.6 ppm for (2) δ−116.2 ppm.

HRMS (3) Calcd for C$_{18}$H$_{19}$NO$_2$FCl: 335.1089; Found: 335.1089.

Anal. Calcd for Cl: 19.05 Found: 19.04

HRMS (2) Calcd for C$_{18}$H$_{20}$NO$_2$F: 301.1497; Found: 301.1432.

EXAMPLE 2

17-Methyl-4,5-epoxy-6,6-difluoro-3-methoxymorphinan Hydrochloride (4) and 17-Methyl-6,7-didehydro-4,5-epoxy-6-fluoro-3-methoxymorphinan (5)

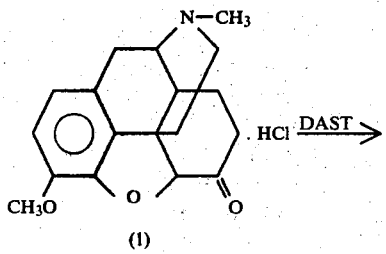

(1)

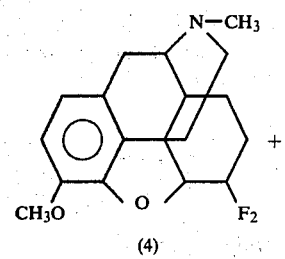

(4)

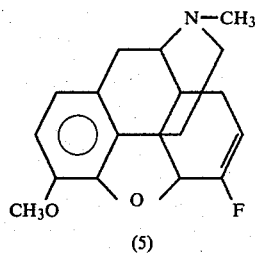

(5)

A mixture of 10.0 g (0.029 mole) of hydrocodone hydrochloride in 200 ml of CCl$_3$F (Freon® 11) was cooled to −78°. To this was added dropwise a solution of 50 ml of diethylaminosulfur trifluoride (DAST) in 50 ml of CCl$_3$F. The mixture was warmed to room temperature, stirred for 5 days, then poured over crushed ice. The solution was made basic with sodium bicarbonate and separated. The aqueous layer was extracted with methylene chloride and the combined organic extracts were washed with water, then brine and dried (MgSO$_4$). This gave 8.65 g of the crude product as a viscous oil. A 1.6 g sample was fractionated by preparative chromatography to give 800 mg of the pure difluoro derivative (4). A sample converted to the hydrochloride salt melted at 270°–275°. $^{19}$F nmr (CDCl$_3$) δ−91.6, −94.2, −104.1 and −106.7 ppm.

The reaction mixture also contained minor amounts of the monofluoro-α,β-unsaturated compound (5).

EXAMPLE 3

I.

17-Cyclobutylcarbonyl-4,5-epoxy-6,6-difluoro-3-methoxymorphinan (7) and 17-Cyclobutylcarbonyl-6,7-didehydro-4,5-epoxy-6-fluoro-3-methoxymorphinan (8)

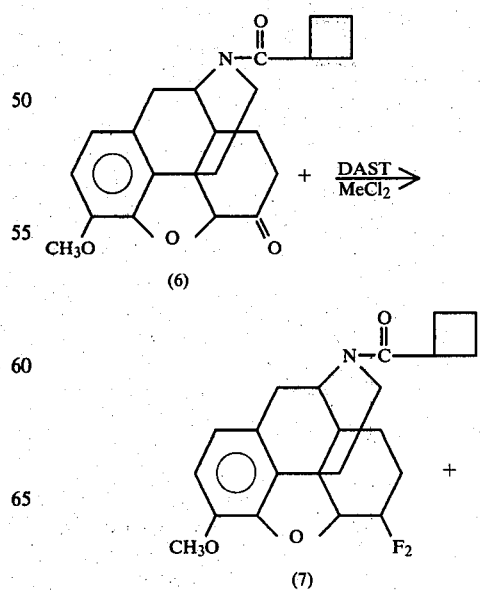

(6)

(7)

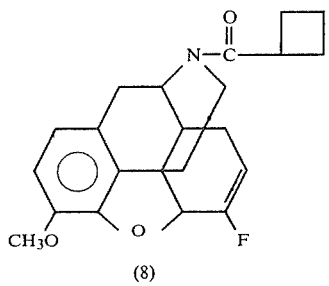

(8)

A solution of 25.0 g (68 mmoles) of the keto amide (6) prepared by reaction of cyclobutyl carbonyl chloride with the amine as described in Example 6 in 200 ml of dry methylene chloride was cooled to −78°. To this was added dropwise a solution of 25 ml (200 mmoles) of DAST in 100 ml dry methylene chloride. The mixture was stirred at 25° for 6 days, poured onto crushed ice and neutralized, separated, washed with water then brine and dried over MgSO$_4$. The resulting oil was collected with ether to give 14.32 g of white solid. Concentration of the ether filtrate gave an additional 10.0 g of solid. $^{19}$F nmr (CDCl$_3$): δ−91.6, −94.2, −104.3 and −106.9 ppm (—CF$_2$) and −116.4 ppm (=CF).

II.

17-Cyclobutylmethyl-4,5-epoxy-6,6-difluoro-3-methoxymorphinan Hydrochloride (9)

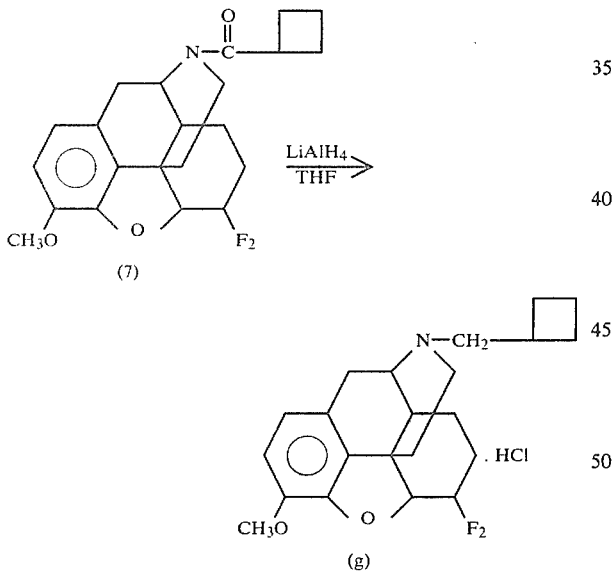

A mixture of 12.2 g of the amides from part I in 100 ml of anhydrous tetrahydrofuran was added dropwise to a stirred suspension of 4.5 g of LiAlH$_4$ in 200 ml of anhydrous tetrahydrofuran. The mixture was heated at reflux for 24 hr, and then hydrolyzed using 4.5 ml water, 4.5 ml of 15% sodium hydroxide and 13.5 ml water. This gave 6.1 g of the crude amines. A 2.2 g sample was chromatographed on silica gel. Elution with methylene chloride containing 2% methanol and 1% diethylamine gave 1.5 g of 90% pure difluoride as a viscous oil. This was dissolved in ether and converted to the hydrochloride salt. $^{19}$F nmr (CDCl$_3$) δ−91.7, −94.3, −104.2 and −106.8 ppm (S). Infrared spectrum showed

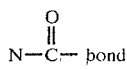

absent.

HRMS: Calcd for C$_{22}$H$_{27}$NO$_2$F$_2$: 375.2008; Found: 375.2003.

EXAMPLE 4

I.

17-Cyclopropylcarbonyl-4,5-epoxy-6,6-14β-trifluoro-3-methoxymorphinan (11) and
17-Cyclopropylcarbonyl-6,7-didehydro-4,5-epoxy-6,14β-difluoro-3-methoxymorphinan (12)

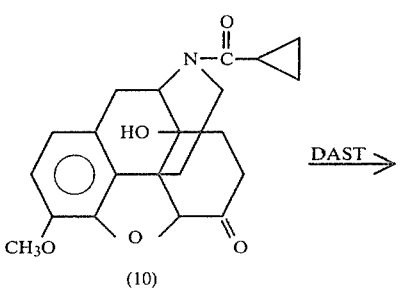

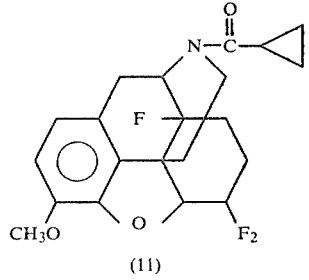

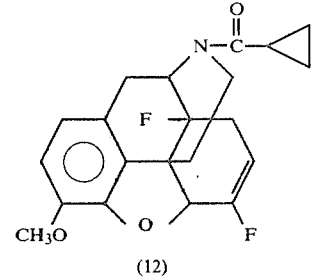

A solution of 24.5 g (0.06 mole) of the ketoamide (10) of dry methylene chloride was cooled to −78°. A solution of 25.0 ml (0.2 mmole) of DAST in 50 ml of methylene chloride was added dropwise. The reaction mixture was stirred at 25° for 4 days then poured over ice and neutralized with sodium bicarbonate. The organic layer was separated, washed with brine and dried (K$_2$CO$_3$). The residual crude product, 23.6 g, was used directly in the next step without further precipitation. Infrared spectrum shows the

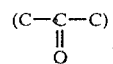

carbonyl bond to be absent.

II.

17-Cyclopropylmethyl-4,5-epoxy-6,6,14β-trifluoro-3-methoxymorphinan Hydrochloride (13)

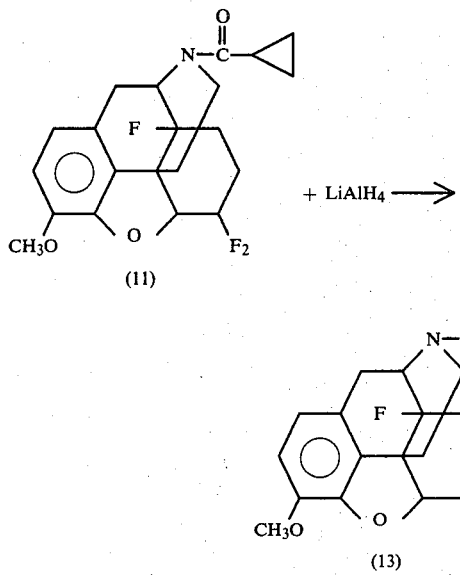

The product from Part I (23.6 g) in 600 ml of anhydrous tetrahydrofuran was treated with 10.0 g of lithium aluminum hydride and refluxed for 18 hr. The reaction was hydrolyzed with 10 ml of water, 10 ml of 15% sodium hydroxide solution and finally with 30 ml of water. The inorganic salts were filtered and the filtrate was concentrated to give 14.2 g of the product as a viscous oil. A 10.1 g sample was chromatographed on florisil. Elution with 10% acetone-hexane gave 3.77 g of the trifluoride and 2.4 g of a mixture of the di- and trifluorides. The trifluoride was triturated with hexane to give a white solid melting at 89°–91°. A sample was dissolved in ether and converted to the hydrochloride salt mp 160°–165°. HPLC showed one major spot (96%). Infrared showed the spectrum

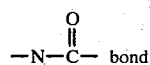

to be absent. $^{19}F$ nmr (CDCl$_3$): δ −91.3, −94.0 and −103.5 ppm (—CF$_2$) and −163.5 ppm (—C—F).

Anal. Calcd for $C_{21}H_{24}NO_2F_3$: C, 66.48; H, 6.38; N, 3.69; F, 15.02; Found: C, 67.25; H, 6.37; N, 3.68; F, 14.89.

HRMS Calcd: 379.1758: Found: 379.1721.

EXAMPLE 5

I.

17-Cyclobutylcarbonyl-4,5α-epoxy-6,6-14β-trifluoro-3-methoxymorphinan (15) and
17-Cyclobutylcarbonyl-6,7-didehydro-4,5α-epoxy-6,14β-difluoro-3-methoxymorphinan (16)

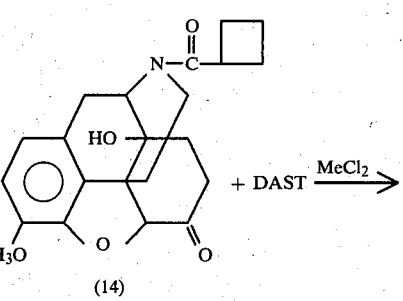

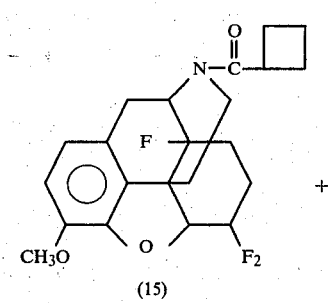

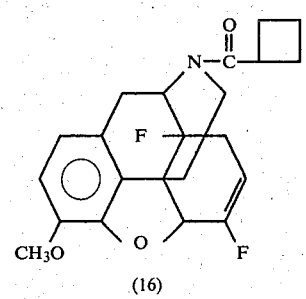

A solution of 18.5 g of the cyclobutyl ketoamide in 100 ml of dry methylene chloride was cooled to −78°. Then a solution of 18 ml of DAST in 50 ml of dry methylene chloride was added dropwise. The mixture was stirred at 25° for 3 days, poured over ice, neutralized with sodium bicarbonate and separated. The organic layer was washed with brine, dried (K$_2$CO$_3$) and concentrated. This gave 19.7 g of the fluoro derivatives as a viscous oil. The oil was triturated with ether. This gave 3.6 g of the trifluoro derivative (15) (by comparative thin layer chromatography) as a white solid melting at 187°–191°. A sample recrystallized from ethyl acetate melted at 194°–195°. HPLC showed one spot (96%). The ether soluble portion was a mixture of the two fluoro derivatives with the major constituent being the 6,6-difluoro.

II.

17-Cyclobutylmethyl-4,5α-epoxy-6,6,14β-trifluoro-3-methoxymorphinan Hydrochloride (17)

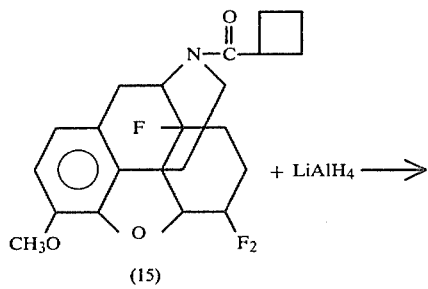

A solution of 2.7 g (6.6 mmoles) of the amide (15) in 75 ml of anhydrous tetrahydrofuran was added dropwise to a stirred suspension of 1.2 g (31.5 mmoles) of lithium aluminum hydride in 75 ml of anhydrous tetrahydrofuran. The mixture was heated at reflux for 24 hrs and hydrolyzed as in the preceding example. This gave 2.6 g (85%) of the trifluoro derivative as a viscous, colorless oil. The oil was dissolved in ether and converted to the hydrochloride salt which was then recrystallized from ethyl acetate. The infrared spectrum showed the absence of the

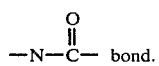
bond.

$^{19}$F nmr (CDCl$_3$) δ=91.3, −94.0 and −103.6, −106.2 ppm (—CF$_2$) and −163.6 ppm (—C—F).

HRMS Calcd. for C$_{22}$H$_{26}$O$_2$NF$_3$: 393.1916; Found: 393.1936.

When the process of Example 5 II is applied to product (16), there is produced 17-cyclobutylmethyl-6,7-didehydro-4,5α-epoxy-6,14β-difluoro-3-methoxymorphinan.

EXAMPLE 6

17-Cyclopropylmethyl-4,5-epoxy-6,6-difluoro-3-methoxymorphinan (22) and 17-Cyclopropylmethyl-6,7-didehydro-4,5-epoxy-6-fluoro-3-methoxymorphinan (23) and Hydrochlorides

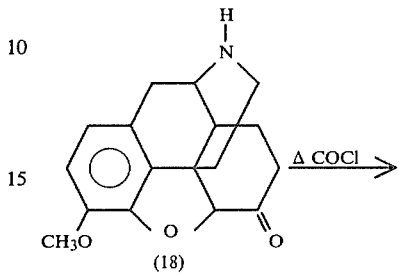

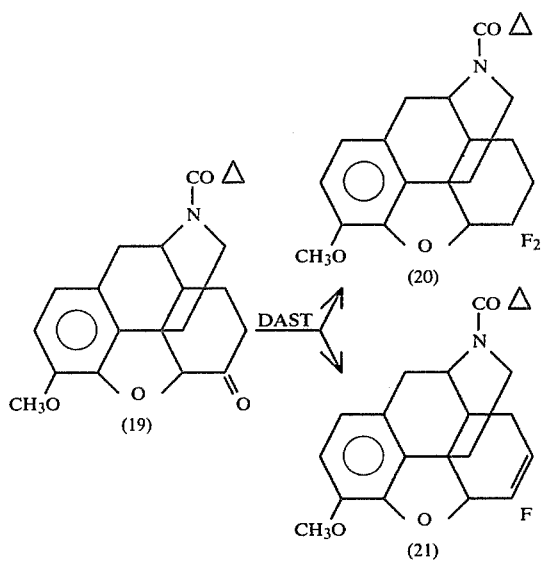

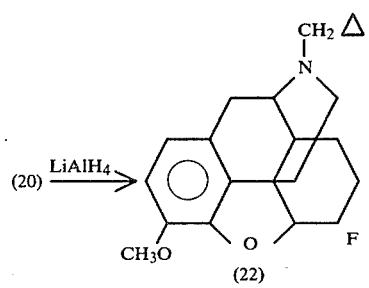

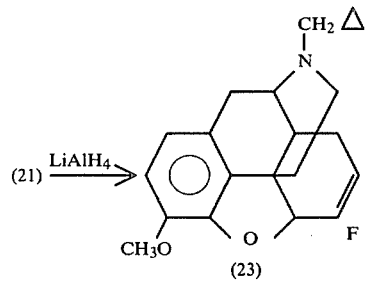

The N-cyclopropylcarbonylcodone (19) was obtained by reacting 18 g of cyclopropane carbonyl chloride with 30.7 g of the amine (18) at room temperature in methylene chloride in the presence of 20 g of tetraethylamine to yield 33 g of product as a white solid.

These are described by Gates, J. Med. Chem. 7, 127 (1964).

When 18.5 g of the amide (19% was dissolved in 150 ml of methylene chloride, cooled, and 18 ml of DAST added, after 3 days at room temperature, 19.2 g of a brown oil resulted. This was dissolved in ether, filtered and the oil chromatographed twice on silica using 90% ether-cyclohexanone with 1% methylene chloride and 0.001% water. There was obtained 4.2 g of 87% pure difluoride (20) and 6.8 g of about a 50:50 mixture of difluoride (20) and monofluoro (21).

A total of 7 g of the amide (20) was dissolved in 100 ml of tetrahydrofuran and mixed with 3 g of LiAlH$_4$ in 100 ml of tetrahydrofuran. After refluxing 16 hrs, 3 ml of water was added followed by 3 ml of 15% NaOH and 9 ml of water to give 6.13 g of product which was chromatographed using 1:1 hexane: acetone containing 1% triethylamine to give 3.6 g of (22) in 96% purity by $^{19}$F nmr or 91% by HPLC as a white solid m.p. 69°-73°. The hydrochloride of the latter softened at 100° and a mp of 123°-133°. HMRS Calcd: 361.1852; Found: 361.1846.

Ten g of codone amide (19) was dissolved in 120 ml of glyme, 0.8 ml sulfuric acid and 10 ml DAST in 80 ml of glyme added at −78° C. After stirring at room temperature for 6 days, the mixture was poured on ice, neutralized, extracted with methylene chloride, evaporated and the residue dissolved in ether to give 10.2 g of the 6-fluoro morphinan (21) which was chromatographed on silica using 90% ether-hexane with 1% methylene chloride and 0.1% water. About 2.3 g of this product was dissolved in 50 ml of tetrahydrofuran and reduced with 1.1 g of LiAlH$_4$ in 50 ml of tetrahydrofuran by refluxing 16 hrs. There was obtained 1.4 g of white product (23) as the HCl salt, mp 93°-97°.

EXAMPLE 7

17-Allyl-4,5-epoxy-6,6-difluoro-3-methoxymorphinan (25) and
17-Allyl-6,7-didehydro-4,5-epoxy-6-fluoro-3-methoxymorphinan (26) and Hydrochlorides

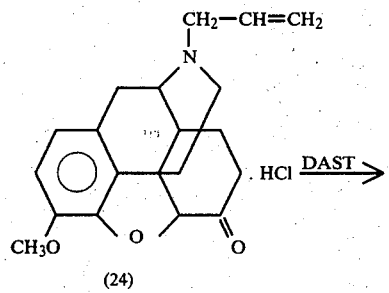

(24)

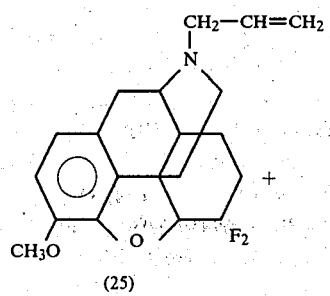

(25)

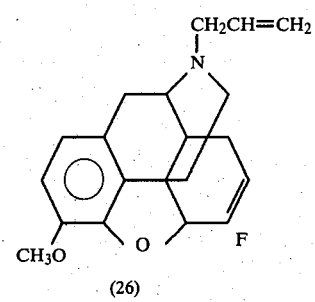

(26)

To 10 g of amine (18) of Example 6 in 150 ml of dimethylformamide was added 4 g of allyl bromide and 2.8 g of NaHCO$_3$. The mixture was heated at 80°-85° for 5 hrs, diluted with water, extracted with ether and converted to 12.7 g of the amine salt (24) above. The salt was reacted with diethylaminosulfur trifluoride according to the process of Example 2 and the hydrochloride salts formed are separated by chromatography as described in Example 6. $^{19}$F nmr (CDCl$_3$): δ−91.6, −94,2, −104.1 and 10.67 ppm.

EXAMPLE 8

A.

17-Cyclobutylcarbonyl-4,5α-epoxy-6-keto-14β-acetyl-3-methoxymorphinan

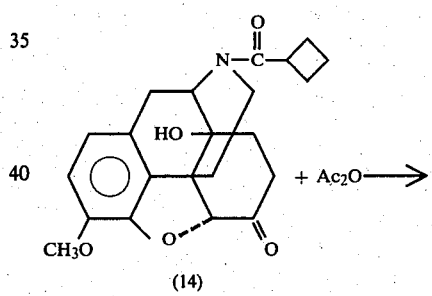

(14)

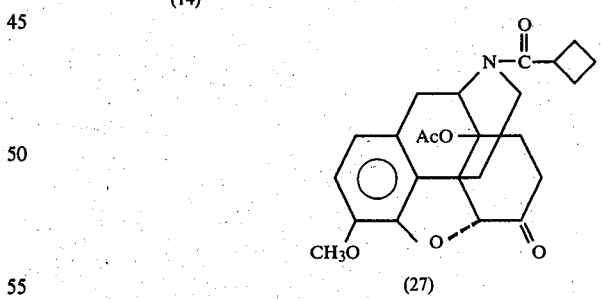

(27)

A solution of 23.0 g of the morphinan (14) in 100 ml of acetic anhydride was heated at reflux for 0.5 hr, cooled and then concentrated. The residue was dissolved in 200 ml of water, cooled to 0° and adjusted to pH 9 with ammonium hydroxide. A viscous oil precipitated. The water layer was decanted and the oil was dissolved in methylene chloride and dried over Na$_2$SO$_4$. Concentration of the methylene chloride gave 22.3 g of viscous oil. The infrared spectrum showed essentially no OH$^-$ absorption.

B.
Cyclobutylcarbonyl-4,5α-epoxy-6,6-difluoro-14β-acetyl-3-methoxymorphinan and
17-Cyclobutylcarbonyl-6,7-didehydro-4,5α-epoxy-6-fluoro-14-acetyl-3-methoxymorphinan

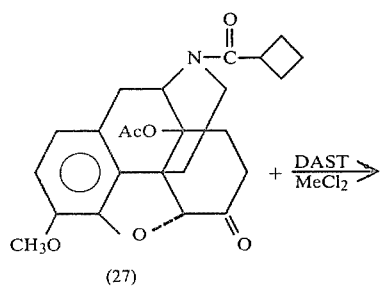

(27)

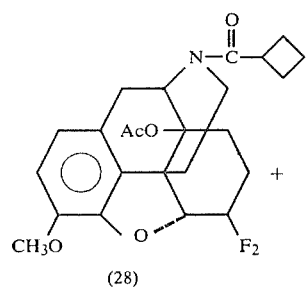

(28)

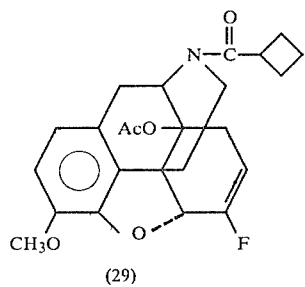

(29)

A solution of 18.0 g of the ketoamide (27) in 150 ml dry methylene chloride was cooled to −78°. A solution of 18 ml of DAST in 150 ml of methylene chloride was added dropwise. The reaction mixture was stirred at room temperature for three days, poured over ice and neutralized with sodium bicarbonate. The organic layer was separated, washed with brine and dried ($K_2CO_3$). This gave 16.6 g of the crude fluorides as a viscous oil. The HRMS of the crude sample showed:

$C_{24}H_{27}NO_5F_2$ Calcd. 447.1856; Found 447.1846.

$C_{24}H_{26}NO_5F$ Calcd. 427.1793; Found 427.1752.

The fluoro derivatives were separated using HPLC. Elution with hexane-acetone-triethylamine gave 8 g of the difluoride (28) as a colorless viscous oil. $^{19}$Fnmr ($CDCl_3$)δ−91.3, −93.9 and 102.3, 104.4 ppm (—$CF_2$).

C.
17-Cyclobutylmethyl-4,5α-epoxy-6,6-difluoro-14β-hydroxy-3-methoxymorphinan Hydrochloride An 8 g sample of the difluoro amide (28) was reduced as in Example 3, II. This gave 4.5 g of tan solid which was dissolved in ether and some insoluble solid was filtered. Concentration of the ether soluble material gave 2.6 g of pale yellow solid which was taken in ether and decolorized by use of charcoal to give a white solid melting at 162°–164°. When converted to the hydrochloride salt (ether) the difluoro morphinan (30) melted at 266°–269°. Its infrared spectrum shows hydroxyl band at 3400 $cm^{-1}$ but no amide or carbonyl absorption.

EXAMPLE 9

17-Cyclopropylmethyl-4,5α-epoxy-6,6-difluoro-14β-hydroxy-3-methoxy morphinan Hydrochloride This compound was prepared using the procedure outlined above starting with (10) and acetylating, fluorinating with DAST, recovering th difluoride and hydrolyzing and reducing as in Example 8 to give the hydrochloride salt, (30) which melted at 248°–252°.

Anal. Calcd for $C_{24}H_{25}NO_3F_2$: C, 66.83; H, 6.68; N, 3.71; Found: C, 66.47; H, 6.64 N, 3.97.

When the general procedure of foregoing Examples 4 and 5 is applied to the corresponding compound where R is

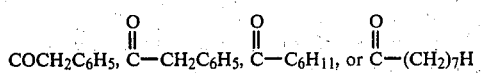

there are obtained the corresponding compounds, e.g., N-phenethyl-6,7-didehydro-4,5α-epoxy-6-fluoro-3-methoxymorphinan, N-phenethyl-4,5α-epoxy-6,6-difluoro-3-methoxymorphinan and the N-cyclohexylmethyl or N-n-octyl morphinans i.e., both the trifluoro and didehydrodifluoro result.

Starting with N-butyl or N-dimethylallylcodeine and using the process of Examples 1 and 2 there results the corresponding butyl and dimethylallyl derivatives. Similarly, N-furanylmethyl, thienylmethyl and thienylethyl compounds corresponding to those of Example 6 can be prepared and used as described above.

N-cyclobutanoylnoroxycodone-14-acetate is used according to the general procedure of Examples 4 and 5, to give both 6,6-difluoro- and 6-fluoro-Δ6,7-cyclobutylmethylnoroxycodone-14-acetate. Hydrolysis of the latter gives the 14-hydroxy compounds. The corresponding 14-butanoyl, propionyl and formyl can be prepared by suitable acylation of the 14-hydroxy compounds.

In the compounds as obtainable by the above procedures, the 3-position is generally the 3-methoxy. Treatment of these compounds with demethylating agents such as hydrogen halides gives the 3-hydroxy from which $C_{2-4}$ alkyl ethers or esters of $C_1$-$C_4$ alkanoic acids can be obtained by general synthetic methods.

Utility

The compounds of this invention are intermediates for compounds that are active pharmaceutically as analgesics and/or narcotic antagonists, as described in the concurrently filed application Ser. No. 944,197 to Boswell and Henderson CR 7833.

Test Results

A standard procedure for detecting and comparing the analgesic activity of compounds for which there is good correlation with human efficacy is the standard phenylquinone writhing test modified from Siegmund, et. al., Proc. Soc. Exp. Biol. Med. 95, 729 (1957). A test compound suspended in 1% methylcellulose was given orally to fasted (17–21 hours) female white mice, 5–20 animals per double blind test. Aqueous (0.01% phenyl-p-benzoquinone) phenylquinone was injected intraperitoneally at 24 minutes later using 0.20 ml per mouse. Commercing at 30 minutes after the oral administration of the test compound, the mice were observed for 10 minutes for a characteristic stretching or writhing syndrome which is indicative of pain induced by phenylquinone. The effective analgesic dose for 50% of the mice (ED 50) was calculated by the moving average method of Thompson, U. R., Bact. Rev. 11 115–145 (1947). This is reported as PQW ED$_{50}$ in the table below.

Narcotic analgesics produce in mice an erection and arching of the tail (90° or more) which is referable to spinal cord stimulation. This Straub tail reaction is not produced by other analgesics, including the narcotic antagonists.

The method used was modified from Shemano (Shemano, I., and Wendel, H., Tox. Appl. Pharm. 6, 334–9 (1964)). CF$_1$S female mice (18–21 g), 10–20 mice per dose were injected subcutaneously with log scaled doses of analgesic in 0.9% saline or 0.45% saline containing 0.5% methylcellulose. A positive Straub tail response was recorded if a tail was erected for 3 seconds at any time within 25 minutes after dosing. A quantal Straub tail ED$_{50}$ was calculated by the moving average method and is an indication of physical dependence.

The narcotic antagonist (anti-Straub tail) property of the compounds is estimated by their ability to prevent morphine-induced Straub tail in mice. In this test the compound is injected intraperitoneally into mice and 10 minutes later 53 mg/kg of morphine sulfate is given subcontaneously. Prevention of the induction of a 90° Straub tail for minutes after the morphine sulfate injection is considered to indicate narcotic antagonism in the compound tested.

The following table shows the activity in mg/kg exhibited by various compounds including those produced from compounds of this invention, when tested by the procedures given above. A value of 135 mg/kg or higher is considered to indicate an inactive compound.

| EXAMPLE | COMPOUND NUMBER | MOUSE ED$_{50}$ VALUES | | |
|---|---|---|---|---|
| | | PQW | STRAUB TAIL | ANTI-STRAUB TAIL |
| 1 | 2 | 8.0 | 26.0 | 94.0 |
| 2 | 4 | 2.7 | 10.0 | >81.0 |
| 3 | 9 | 2.9** | >135.0 | 4.1 |
| 4 | 13 | >135.0 | >135.0 | N.T. |
| 5 | 17 | >135.0 | >135.0 | 17.0 |
| 6 | 22 | 2.2** | >54.0 | 0.15 |
| 6 | 23 | 18. | >135.0 | 0.21 |
| 8 | 30 | 26.0 | >135.0 | 10.8 |
| Codeine PO$_4$ | | 4.7** | 202.0 | >140.0 |
| Morphine SO$_4$ | | 3.0** | 48.0 | N.T. |
| Ayer 3,137,701 (6-fluoro-7,8 double bond) | | 32.0 | 63.0 | >162.0 |

N.T. = Not Tested
**= Peak time value (maximum activity within 30 minutes of administration).

What is claimed is:

1. Process of reacting under substantially anhydrous conditions the ketone having the formula

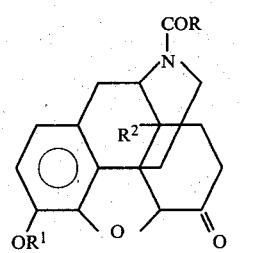

or

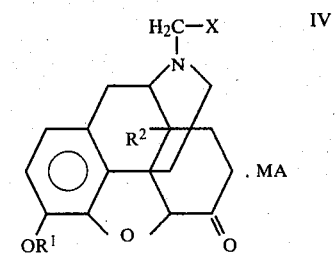

wherein
X is H or R;
R is selected from the group consisting of alkyl of 1–5 carbon atoms, vinyl, 1-propenyl, isobutenyl, cycloalkyl of 3–6 carbon atoms, furanyl, thienyl, thienylmethyl and phenylmethyl which may be ring substituted with chloro, bromo, fluoro or 1–3 carbon atom alkyl substituents;

$R^1$ is selected from the group consisting of alkyl of 1–4 carbon atoms, alkanoyl of 1–4 carbon atoms;

$R^2$ is selected from the group consisting of hydrogen, fluorine, hydroxy and alkanoyloxy of 1–4 carbon atoms; and MA is a mineral acid, with a disubstituted aminosulfur trifluoride fluorinating agent of the formula $R^3R^4NSF_3$ wherein each $R^3$ and $R^4$, alike or different, is a primary alkyl group of 1–4 carbon atoms; or $R^3$ and $R^4$ when taken together are $-(CH_2)_4-$, $-(CH_2)_5-$ or $-CH_2CH_2OCH_2CH_2-$; at a temperature of about $-40°$ C. to about $+80°$ C.; in the presence of a polar or nonpolar solvent; and recovering the fluorine-containing compound having the formula

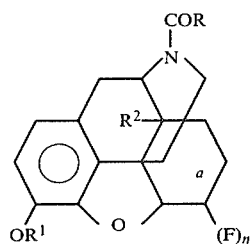   I when the ketone is of formula II, and having the formula

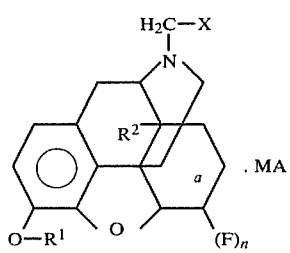   V when the ketone is of formula IV,
wherein said formulas I and V
X, R, $R^1$, $R^2$ and MA are as defined above;
n is 1 or 2; and
a is a 6,7 double bond when n is 1 and a single bond when n is 2.

2. The process of claim 1 in which the ketone of formula IV is reacted.

3. The process of claim 1 in which the ketone of formula II is reacted and the fluorine-containing compound thus produced is reduced the convert the >NCOR group to >NCH$_2$R.

4. The process of claim 3 in which the reduction is accomplished with LiAlH$_4$.

5. The process of claim 1 in which the starting ketone is hydrocodone hydrochloride, the fluorinating agent is diethylaminosulfur trifluoride, and the solvent is ethylene glycol methyl ether.

6. The process of claim 1 in which the fluorinating agent is diethylaminosulfur trifluoride and the solvent is fluorotrichloromethane.

7. The process of claim 1 in which the fluorinating agent is diethylaminosulfur trifluoride and the solvent is methylene chloride.

8. Compound of the formula

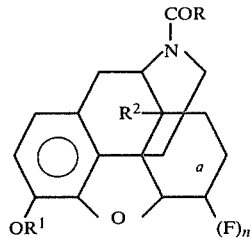

wherein
R is selected from the group consisting of alkyl of 1–5 carbon atoms, vinyl, 1-propenyl, isobutenyl, cycloalkyl of 3–6 carbon atoms, furanyl, thienyl, thienylmethyl and phenylmethyl which may be ring substituted with chloro, bromo, fluoro, or 1–3 carbon atom substituents;
$R^1$ is selected from the group consisting of alkyl of 1–4 carbon atoms and alkanoyl of 1–4 carbon atoms;
$R^2$ is selected from the group consisting of hydrogen, fluorine, hydroxy and alkanoyloxy of 1–4 carbon atoms;
n is 1 or 2; and
a is a 6,7 double bond when n=1, and a single bond when n=2.

* * * * *

UNITED STATES PATENT AND TRADEMARK OFFICE
CERTIFICATE OF CORRECTION

PATENT NO. : 4,236,008

DATED : November 25, 1980

INVENTOR(S) : Rosetta M. Henderson

It is certified that error appears in the above—identified patent and that said Letters Patent is hereby corrected as shown below:

Column 20, end of line 23, insert -- I --.

Signed and Sealed this

Twenty-first Day of July 1981

[SEAL]

Attest:

Attesting Officer

GERALD J. MOSSINGHOFF

Commissioner of Patents and Trademarks